US010506955B2

(12) United States Patent
Tholl et al.

(10) Patent No.: US 10,506,955 B2
(45) Date of Patent: Dec. 17, 2019

(54) METHOD AND APPARATUS FOR NON-INVASIVE DETERMINATION OF A MEASURED VARIABLE OF AN ANALYTE IN A BIOLOGICAL BODY

(71) Applicant: SAMTD GMBH & CO. KG, Nuremberg (DE)

(72) Inventors: Hans Dieter Tholl, Salem (DE); Mathias Glasmacher, Reilingen (DE)

(73) Assignee: SAMTD GmbH & Co. KG, Nuremberg (DE)

( * ) Notice: Subject to any disclaimer, the term of this patent is extended or adjusted under 35 U.S.C. 154(b) by 715 days.

(21) Appl. No.: 15/132,279

(22) Filed: Apr. 19, 2016

(65) Prior Publication Data
US 2016/0338623 A1 Nov. 24, 2016

(30) Foreign Application Priority Data

May 19, 2015 (DE) .................. 10 2015 006 406

(51) Int. Cl.
*A61B 5/1455* (2006.01)
*A61B 5/145* (2006.01)
(Continued)

(52) U.S. Cl.
CPC .......... *A61B 5/1455* (2013.01); *A61B 5/0066* (2013.01); *A61B 5/14532* (2013.01); *A61B 5/02416* (2013.01); *A61B 5/14546* (2013.01)

(58) Field of Classification Search
None
See application file for complete search history.

(56) References Cited

U.S. PATENT DOCUMENTS 4,743,107 A 5/1988 Aizu et al.
8,277,384 B2 10/2012 Fine
(Continued)

FOREIGN PATENT DOCUMENTS

EP 0234869 A2 9/1987
EP 2799010 A1 11/2014
(Continued)

OTHER PUBLICATIONS

M.A. Pleitez et al., "In Vivo Noninvasive Monotoring of Glucose Concentration in Human Epidermis by Mid-Infrared Pulsed Photoacoustic Spectroscopy", Analytical Chemistry 2013, vol. 85(2), pp. 1013-1020.
(Continued)

*Primary Examiner* — Eric F Winakur
*Assistant Examiner* — Marjan Fardanesh
(74) *Attorney, Agent, or Firm* — Laurence A. Greenberg; Werner H. Stemer; Ralph E. Locher

(57) ABSTRACT

A method and apparatus for non-invasive determination of a measured variable of an analyte in a biological body. The body is irradiated locally by light in an automatic manner from a wavelength range matched to an absorption signature of the analyte. At least some of the light penetrates into the body and is absorbed by the analyte. The body heats up at least locally as a result of the absorption by the analyte and a consequently occurring change in a speckle pattern of coherent light scattered at the body is detected. A value of the measured variable of the analyte is deduced from the detected change in the speckle pattern. In particular, the concentration of glucose is established in a non-invasive manner as a measured variable.

31 Claims, 1 Drawing Sheet

(51) Int. Cl.
*A61B 5/00* (2006.01)
*A61B 5/024* (2006.01)

(56) References Cited

U.S. PATENT DOCUMENTS

| | | |
|---|---|---|
| 2002/0016533 A1 | 2/2002 | Marchitto et al. |
| 2009/0209834 A1 | 8/2009 | Fine |
| 2012/0277559 A1 | 11/2012 | Kohl-Bareis et al. |
| 2014/0206980 A1 | 7/2014 | Lee et al. |
| 2016/0356746 A1* | 12/2016 | Piestun ............. A61B 5/0095 |
| 2017/0209047 A1 | 7/2017 | Zalevsky et al. |

FOREIGN PATENT DOCUMENTS

| | | |
|---|---|---|
| WO | 0150955 A1 | 7/2001 |
| WO | 2014020611 A1 | 2/2014 |
| WO | 2014116483 A1 | 7/2014 |

OTHER PUBLICATIONS

Z. Zalevsky et al., "Laserbasierte biomedizinishe Untersuchungen-simultan and kontaktlos [Laser-based biomedical examinations—simultaneous and contactless]" BioPhotonic 3, 2012, pp. 30-33—Statement of Relevance.

N. Ozana et al., "Improved noncontact optical sensor for detection of glucose concentration and indication of dehydration level", Biomedical Optics Express 2014, vol. 5, No. 6, pp. 1926-1940.

K.-U Jagemann et al., "Application of Near-Infrared Spectroscopy for Non-Invasive Determination of Blood/Tissue Glucose Using Neural Networks", Zeitschrift fuer Physikalische Chemie, vol. 191, 1995, pp. 179-190.

K. Yamakoshi et al., "Pulse Glucometry: A new Approach for Non-invasive Blood Glucose Measurement Using Instantaneous Differential Near Infrared Spectrophotometry", Journal of Biomedical Optics, vol. 11(5), 2006, pp. 1-11.

Xinxin Guo et al. "Noninvasive glucose detection in human skin using wavelength modulated differential laser photothermal radiometry", Biomedical Optics Express, vol. 3 (11), 2012, pp. 3012-3021.

Beiderman, Y., et al., "Demonstration of remote optical measurement configuration that correlates to glucose concentration in blood", Biomedical Optics Express, Apr. 1, 2011, pp. 858-870, vol. 2, No. 4, URL: http://www.ncbi.nlm.nih.gov/pmc/articles/PMC3072081/.

* cited by examiner

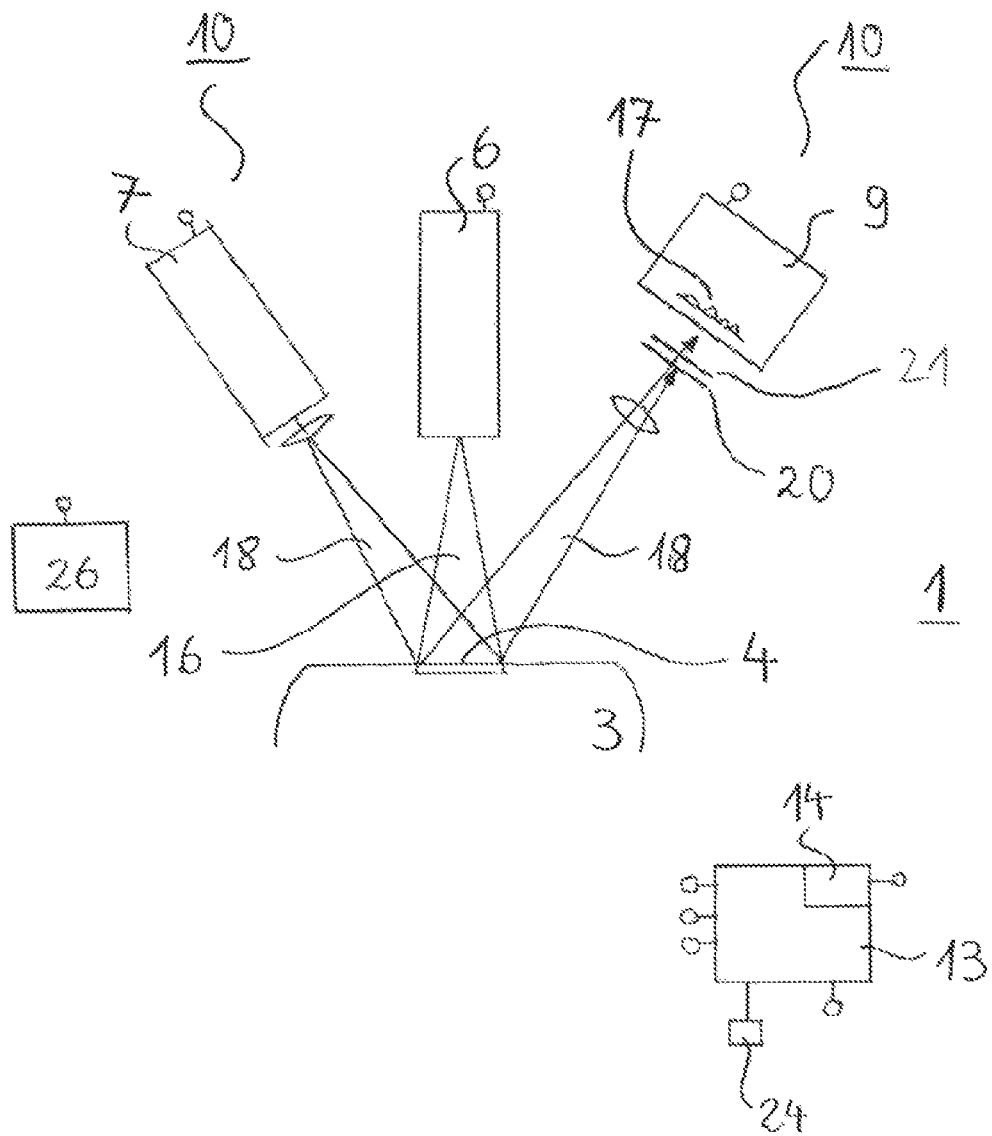

METHOD AND APPARATUS FOR NON-INVASIVE DETERMINATION OF A MEASURED VARIABLE OF AN ANALYTE IN A BIOLOGICAL BODY

CROSS-REFERENCE TO RELATED APPLICATION

This application claims the priority, under 35 U.S.C. § 119, of German application DE 10 2015 006 406.1, filed May 19, 2015; the prior application is herewith incorporated by reference in its entirety.

BACKGROUND OF THE INVENTION

Field of the Invention

The invention relates to a method for non-invasive determination of a measured variable of an analyte in a biological body, wherein, in an automated manner, the body is irradiated locally by light from a wavelength range matched to an absorption signature of the analyte. At least some of the light penetrates into the body and is absorbed by the analyte. The invention furthermore relates to an apparatus embodied appropriately for carrying out the method. In particular, the invention considers a non-invasive determination of a glucose level.

In principle, it is desirable to be able to determine biomedical parameters in vivo and non-invasively. Using this, it is possible, in particular, to establish parameters, which are required for a diagnosis and which should be monitored repeatedly or frequently, in a pain-free manner and without intervention on a human or animal body. However, precisely a non-invasive determination of a measured variable of an analyte contained in the body is difficult as obtaining measurement signals assignable specifically to an analyte is made more difficult by the multiplicity of structures of a biological body which differ in terms of the physical and chemical parameters thereof, such as e.g. the skin, muscles, tendons, bones, vessels, fatty tissue and organ tissue. Moreover, measurement signals from the interior of the body have, as a matter of principle, a comparatively poor signal-to-noise ratio. If the measured variable of the analyte needs to be established for a specific structure, for example in a blood vessel, the measurement result is additionally falsified by the surroundings if the measured variable of the analyte has a different value there. By way of example, analytes of interest are sugars, in particular glucose, alcohol, drugs, fats and water, but also hormones, messengers, enzymes, trace elements, minerals, metals, medicaments and toxic substances. In this case, the analytes can be present in solid, gaseous or liquid form, wherein, in particular, the analyte can be given as a solution in bodily fluids or in body tissue.

It is well known that optical methods are particularly suitable for non-invasive establishment of biomedical parameters; these are able to detect the presence of the sought-after analyte by scattering, transmission, absorption, reflection, polarization, phase change, fluorescence, photoacoustic excitation or photo-thermal excitation. Depending on the method, a value for the desired measured variable, such as e.g. a value for concentration, can be determined from the detection signal with corresponding measurement accuracy. In particular, a measurement signal selective for the analyte, which enables a quantitative detection, can be obtained after specific absorption by radiating-in light with a specific wavelength matched to an absorption signature of the analyte.

By way of example, M. A. Pleitez et al., "In Vivo Noninvasive Monitoring of Glucose Concentration in Human Epidermis by Mid-Infrared Pulsed Photoacoustic Spectroscopy", Analytical Chemistry 2013, volume 85 (2), pages 1013-1020 describes a photoacoustic method for determining the concentration of glucose in the human epidermis. In the process, the skin is irradiated in a pulsed manner in the fingerprint range of glucose by light with wavelengths of between 8 μm and 10 μm, i.e. in the range of the excitation energies of characteristic ring deformation vibrations. Acoustic vibrations emerging from the body, which are created as a consequence of the absorption by glucose contained in interstitial fluid in the tissue, are detected as a measurement signal. In the process, light in this wavelength range penetrates a few 10 μm into the skin such that the glucose contained in the epidermis can be detected in the interstitial water and determined. Z. Zalevsky, J. Garcia, "Laserbasierte biomedizinische Untersuchungen—simultan and konkaktlos [Laser-based biomedical examinations—simultaneous and contactless]", BioPhotonic 3, 2012, pages 30-33 has furthermore disclosed a non-invasive method for determining the alcohol and glucose level in blood, wherein skin vibrations are measured by observing speckle patterns. To this end, the skin is illuminated by a laser and the speckle patterns formed by interferometry are monitored.

In this respect, N. Ozana et al., "Improved noncontact optical sensor for detection of glucose concentration and indication of dehydration level", Biomedical Optics Express 2014, volume 5, number 6, pages 1926-1940 has furthermore proposed to increase the sensitivity of the speckle interferometry for glucose by virtue of a magnetic field being generated in addition to the irradiation of the skin by laser beam, with the optical activity of the glucose molecule being exploited. Vibrations of the skin caused by blood pulses are observed by way of the speckle patterns. The concentration of glucose in the blood is deduced from a maximum offset of the speckle pattern. A comparable method is described in Y. Beiderman et al., "Demonstration of remote optical measurement configuration that correlates to glucose concentration in blood", Biomedical Optics Express, 2011, volume 2, number 4, pages 858-870. Here too, the concentration of glucose in the blood is deduced from the offset in speckle patterns correlated with the pulse or heartbeat. Theoretically, this is explained in that glucose influences the viscosity of the blood, as a result of which the vibrations of the skin caused by the blood pulses exhibit a dependence on the glucose concentration. This dependence can be detected by way of the offset of the speckle patterns.

Furthermore, K.-U. Jagemann et al., "Application of Near-Infrared Spectroscopy for Non-Invasive Determination of Blood/Tissue Glucose Using Neural Networks", Zeitschrift für Physikalische Chemie, volume 191, 1995, pages 179-190 has disclosed a non-invasive determination of glucose in blood or tissue by means of NIR spectroscopy. There, irradiation is carried out using light in the near infrared spectral range. Spectra are observed in diffuse reflection as a measurement signal. In order to improve the measurement signal, K. Yamakoshi et al., "Pulse Glucometry: A new Approach for Non-invasive Blood Glucose Measurement Using Instantaneous Differential Near Infrared Spectrophotometry", Journal of Biomedical Optics, volume 11 (5), 2006, pages 1-11 has furthermore disclosed the practice of correlating NIR spectra with the heartbeat.

Xinxin Guo et al., "Noninvasive glucose detection in human skin using wavelength modulated differential laser photothermal radiometry", Biomedical Optics Express, volume 3 (11), 2012, pages 3012-3021 has furthermore disclosed the practice of establishing the glucose concentration in the skin by means of the photothermal up-conversion process by simultaneously radiating-in laser light with two discrete wavelengths while observing the differential emission spectrum.

The prior art methods for in vivo non-invasive determination of a measured variable of an analyte in a biological body do not reach the sensitivity and specificity desired for clinical applications. Moreover, on account of the complexity of the required measurement apparatuses and on account of the time required for the measurement, some of these methods are not suitable to be considered or used by patients for regular self-monitoring of the corresponding measured variable of the analyte. In particular, there still is no non-invasive method for determining the glucose concentration which people suffering from diabetes could use themselves for regular monitoring at home. Nevertheless, this would be desirable since the previous methods regularly make a possibly painful blood collection necessary or since meaningful measurements repeated at short time intervals are not practical in certain situations.

SUMMARY OF THE INVENTION

It is accordingly an object of the invention to provide a method and an apparatus which overcome the above-mentioned and other disadvantages of the heretofore-known devices and methods of this general type and provide for an alternative non-invasive method for determining a measured variable of an analyte in a biological body, which offers the potential for an application in the consumer market or in clinical routine such that the patient can carry out independent measurements for monitoring the respective measured variable.

Furthermore, the invention is based on the object of specifying a device suitable for carrying out the specified method, which offers the possibility for development into a consumer product or for clinical routine.

With the foregoing and other objects in view there is provided, in accordance with the invention, a method of non-invasive determination of a measured variable of an analyte in a biological body, the method comprising:

locally irradiating the body, in an automated manner, with light having a wavelength range matched to an absorption signature of the analyte;

causing at least some of the light to penetrate into the body and to be absorbed by the analyte, whereupon the body heats up at least locally as a result of an absorption by the analyte;

detecting a consequently occurring change in a speckle pattern of coherent light scattered at the body, and deducing from the change in the speckle pattern a value of the measured variable of the analyte.

In other words, the first-mentioned object is achieved by a method for non-invasive determination of a measured variable of an analyte in a biological body, wherein, in an automated manner, the body is irradiated locally by light from a wavelength range matched to an absorption signature of the analyte, wherein at least some of the light penetrates into the body and is absorbed by the analyte, wherein the body heats up at least locally as a result of the absorption by the analyte and a change in a speckle pattern of coherent light scattered at the body occurring as a result of the absorption is detected, and wherein a value of the measured variable of the analyte is deduced from the detected change in the speckle pattern.

In a first step, the invention proceeds from the idea that the absorption spectrum of an organic analyte in particular differs in a characteristic manner in terms of the fingerprint region thereof, which lies approximately between 6 μm and 16 μm, from the absorption spectrum of water. However, the absorption coefficients of water are also large in this wavelength range. In this respect, only a small portion of the light matched to a characteristic absorption signature in the fingerprint range of the analyte enters into the biological body in order to be able to interact with the lower-lying analyte there. A substantially even smaller portion of light leaves the body as a consequence of the characteristic backscatter connected with the absorption and is available for the detection. Accordingly, the desired measurement signal has, as a matter of principle, a very low signal-to-noise ratio.

In a second step, the invention proceeds from the discovery that observable absorption spectra which are characteristic for the analyte per se lose significance in a scattering, reflection, emission or transmission geometry as a result of the interaction of the observation light with the body. The observation light experiences wavelength-dependent damping. The selectivity in respect of the analyte is reduced.

In third step, the invention leads to the discovery that the problem of the low signal-to-noise ratio and the low selectivity when observing the characteristic absorption of the analyte per se can be circumvented if a speckle pattern which is related to the characteristic absorption is observed. The fact that the biological body warms up at least locally as a result of the specific absorption by the analyte is employed, as a result of which, as a consequence, in particular an at least local deformation of the surface thereof, a change in the scattering properties (scattering coefficient, angle scattering) in layers close to the surface and/or a change in the refractive index in layers close to the surface can be seen. These changes, which are connected specifically with the analyte and, in particular, with the concentration thereof, at the body surface or in layers of the body close to the surface are detected by way of an observed change in the speckle pattern. A value of the measured variable of the analyte can be deduced from this change. Changes in the speckle pattern therefore have a direct relationship with the presence of the analyte, which is queried by way of a specific absorption of the radiated-in light.

By contrast, the methods known from the prior art for in vivo determination of a measured variable of an analyte in a biological body by means of speckle interferometry merely provide for using radiated-in light exclusively for generating the speckle pattern. Changes in the speckle pattern are queried at pulsating skin surfaces. A statement about the measured variable of the analyte to be determined emerges from the observed changes in the speckle pattern as a consequence of the concentration of the analyte in the blood, as a result of which the flow properties of the latter change. However, since the flow properties of blood are not only dependent on the observed analyte, the novel method specified here is substantially more selective. At the same time, it also has a higher sensitivity. Incidentally, the specificity and the sensitivity of the novel method are also improved in relation to the optical methods described at the outset, which query the absorption properties of the analyte.

Incidentally, in the present case, a speckle pattern is understood to mean the pattern with characteristic intensity maxima and intensity minima emerging as a consequence of different phase angles in diffusely scattered or reflected light at the location of the observer in the case of a two-dimensional irradiation of a surface with coherent light. The pattern created by interference is very sensitive to changes of the surface or in layers close to the surface.

Preferably, a range with which a penetration depth into the body suitable for determining the specific analyte is achieved is selected for the wavelength range of the radiated-in light. Preferably, this wavelength range is selected advantageously for a sufficient penetration depth in view of the absorption spectrum of water. In this respect, a suitable wavelength range is the so-called fingerprint range of organic molecules, i.e. the range of the energies of characteristic structure vibrations. Therefore, the body is advantageously irradiated by light from an IR sub-range, in particular from a wavelength range with wavelengths between 6 μm and 16 μm, preferably in the LWIR (long wavelength infrared) range between 8 μm and 15 μm. If glucose is intended to be determined as an analyte, a range between 7 μm and 11 μm, in which the glucose molecule exhibits characteristic ring deformation vibrations, is expediently selected. It is possible to further improve the selectivity of the method by way of a narrowband selection, in particular, of the radiated-in light, which is directed to a specific absorption signature of the analyte.

In a further preferred embodiment, the wavelength of the radiated-in light is varied during the measurement, wherein the change in the speckle pattern is detected for different wavelengths in each case. In particular, the wavelength interval from the lowest to the highest wavelength, provided for the radiated-in light, is passed through and the change in the speckle pattern is preferably recorded repeatedly for each wavelength. As a result of that, the response of the measurement system is established repeatedly in a redundant manner. Additionally, the power density of the radiated-in light can expediently also be varied during the measurement and the change in the speckle pattern can be detected for different power densities. As a result of this, the redundancy or over-determination of the system is further increased. In order to carry out the measurement, image sequences of the speckle pattern at different wavelengths and/or at different power densities in particular are recorded.

Preferably, the change in the speckle pattern is alternately detected at a wavelength in an absorption maximum and at a wavelength between the absorption maxima of the analyte. As a result of a differential evaluation of the observed speckle patterns, it is possible to deduce the measured variable of the analyte to be determined. As a result of this, interference effects can be minimized or removed out of the measurement result by calculation. The measurement at the absorption minimum exhibits artefacts which are not traced back to the presence of the analyte.

In an advantageous further embodiment, the light is radiated-in periodically with a modulation frequency. As a result of this, it is also possible to use differential methods for the evaluation of the measurement signals. The evaluation is then carried out by a difference observation of the speckle pattern when the excitation light is switched on and when the excitation light is switched off. In other words: the specific heating of the body surface is time-modulated by the modulation frequency. Preferably, it is also possible to deduce relaxation times of the body surface after heating took place from an image sequence of the speckle pattern. These decay times can also be used to determine the measured variable of the analyte. In an alternative variant, the specific irradiation of the analyte can be terminated, and the development of the speckle pattern over time can be analysed. This provides a statement about the development of the surface temperature over time. In this case, images of the speckle pattern following one another in an image sequence, as difference images, can be evaluated in respect of a change.

In a particularly suitable measurement method, the detection of the change in the speckle pattern is synchronized with the modulation frequency of the light radiated-in periodically. In this case, the change in the speckle pattern is advantageously obtained from the difference observation of images of the speckle pattern at different phase angles of the light irradiation. Expediently, there is averaging over a plurality of images of the speckle pattern at the same phase angle in this case. Additionally, the power density of the radiated-in light can be modulated over time, as was already described above. As a result of this, the signal-to-noise ratio of the measurement signal can be further improved. The change signal formed then exhibits a modulation in accordance with the modulation frequency of the power density. The information from this modulation can also be used to determine and evaluate the measured variable of the analyte.

Since the heart rate is a further periodic property in a biological body of an animal or human, the detected change in the speckle pattern is preferably correlated, additionally or alternatively, to a heart rate of the biological body. By way of such a method, the pulsating feature of the system as a consequence of the heartbeat is accounted for, which is reflected in varying geometries, pressures and temperatures and in varying concentrations of the analyte emerging therefrom. If the change in the speckle pattern, for example in the case of the modulated on/off irradiation, when varying the optical power density or when varying the wavelength is detected in each case from images at the same phase relation of the heartbeat, such periodic measurement uncertainties are eliminated.

In a further preferred embodiment, an image sequence of speckle patterns is recorded, wherein the change in the speckle pattern is detected by a comparison of images from the recorded image sequence. The images used to detect the change in the speckle pattern are selected from the recorded image sequence in accordance with the respectively employed modulation method of the radiated-in light. In particular, light/dark difference images, which relate to the power density, the wavelength or light, switched on or off, for exciting the analyte, are selected. The largest possible change in the speckle pattern caused by the analyte is to be expected in such difference images, and so such an evaluation has a high specificity and sensitivity for the analyte to be examined. At the same time, illumination artefacts and offset effects are reduced as a result of forming difference images.

Preferably, the change in the speckle pattern is established as a contrast value in a difference image. To this end, an analysis in respect of the standard deviation and in respect of the mean value of the observed pixel values is carried out in the difference image, for example within a selected image portion. In this case, an image recording device, such as e.g. a CCD detector or a digital image recording camera, is expediently used for the purposes of observing the speckle pattern. Both a global and a local contrast can be used in the difference image for evaluation purposes. By way of example, the global contrast can be established as largest greyscale value difference in the recorded image. A local contrast can be calculated as an average greyscale value difference between adjacent pixels in an image region of a predetermined size.

Expediently, the images in the image sequence are recorded with a predetermined image refresh rate, wherein the image refresh rate is synchronized with the modulation frequency of the light radiated-in periodically and/or with the heart rate of the biological body. In this manner, the images of the image sequence have a fixed phase relationship with respect to the modulation of the periodically radiated-in light and/or with respect to the heart rate. By means of this phase relationship, it becomes possible to selectively select images of the image sequence and to use these for evaluating the difference, as a result of which the signal-to-noise ratio of the measurement signal is improved.

In a further preferred embodiment, the change in the speckle pattern from the recorded image sequence is detected as a function of time. As a result of this, it is possible, as already explained above, to obtain statements about relaxation times of the body or of the body surface. As a result of this, the observed system is detected in an over-determined manner, as a result of which the specificity and selectivity in respect of the examined analyte are further improved.

For the purposes of determining the measured variable of the analyte, the contrast in the difference image of the speckle pattern can furthermore be established as a function of the radiated-in wavelength and/or as a function of the modulation index in the case of an additional variation of the power density and can be evaluated accordingly.

The body is preferably irradiated by polarized light in order to further improve the signal-to-noise ratio. As a result of this, the direct Fresnel reflection can be discriminated, for example by the use of a corresponding polarization filter. This is advantageous, in particular, if the selectively radiated-in light is used both for exciting the analyte and for generating the speckle pattern. In this case, no further measurement light source is required in addition to the excitation light source. Speckle patterns would also be generated by the depolarized radiation reflected from deeper body layers. Preferably, use is made of a polarization discriminator or a polarization analysis of the observed light or speckle pattern is carried out when polarized light is radiated-in. As a result, the speckle pattern can be observed in a manner dependent on the polarization of the light scattered at the body and the change in the speckle pattern can be detected in each case for a specific polarization.

Advantageously, a magnetic field is additionally generated at the location where the body is irradiated by light. Such a magnetic field is advantageous if the examined analyte exhibits a comparatively large Faraday effect. Then, the examined analyte brings about a specific rotation of the polarization direction of the radiated-in light when an external magnetic field is present. It is then possible, in conjunction with a polarization analyser or polarization discriminator, to further increase the specificity of the measurement method. In particular, glucose as an analyte exhibits a comparatively large Verdet constant, which is decisive for the angle of rotation of the change in polarization.

Preferably, the body is irradiated using a tunable light source, in particular using a narrowband semiconductor laser. A quantum cascade laser, in particular, is able to emit, in a narrowband, a wavelength within the fingerprint range with a high quality. Simultaneously, such a laser exhibits tunability over approximately 20% of the central wavelength. By way of example, a quantum cascade laser which emits light with a wavelength of between 7 μm and 11 μm in a tunable manner can be used. Characteristic absorption bands of glucose as an analyte that is preferably to be observed lie in this range.

In another variant, a light source emitting over a broadband is used to illuminate the body. By way of example, the wavelength range to be radiated-in in each case can then be selectively selected by filtering. In particular, a source of heat can be used as a light source emitting in the IR range or in an IR sub-range. Such a heat source enables ad hoc radiating-in of a whole wavelength range. However, the intensities of light sources emitting over a broadband are generally lower in comparison with tunable light sources emitting at a specific wavelength and exhibit a lower quality. Moreover, the thermal radiation of the emitting light source must be separated well.

As described, the measurement method for determining the measured variable of an analyte can be carried out using a single light source if the latter emits in an absorption region of the analyte and is also suitable for generating a speckle pattern. This is the case if a first coherent light source is used to generate the light matched to the absorption signature of the analyte and if the speckle pattern is observed in the light of the first light source scattered back from the body. A suitable semiconductor laser satisfies this condition, and so the same light can be used both to excite the analyte and to generate the speckle pattern.

In a further advantageous embodiment, the body is irradiated by light from a second coherent light source, in particular in the visible spectral range, wherein the speckle pattern is observed in the light of the second light source scattered back from the body. In this case, a second light source is used to generate the speckle pattern. Then, only local deformations on the surface of the body are observed by way of the speckle pattern. The light from the first light source can easily be masked from the observed beam path by means of a filter.

Advantageously, glucose is considered as the analyte and the concentration thereof is determined as a measured variable of the glucose. In particular, the method can be applied to the extent of establishing the glucose level, i.e. the concentration of glucose in blood. The wrist, a forearm or a lower leg are particularly suitable for the respective measurement on the body since blood vessels run near the surface there. By radiating-in light in the fingerprint range, vessels (with glucose) in particular are reached via various skin layers without glucose. The respective glucose content in the blood can be deduced by way of the change in the speckle pattern of the skin surface.

Preferably, establishing the value of the measured variable in a specific structure of the body comprises an internal calibration by taking into account at least one further value of the measured variable at a different observation location in the body. In the case of an analyte in the blood, the various concentrations in arteries and veins offer, where necessary, a suitable possibility for a calibration in this case. It is also possible to use the fact that the concentrations of the analyte in the interstitial water and in blood are correlated to one another. Moreover, for the purposes of an internal calibration, particularly in the case of glucose, the patient can take the analyte and it is subsequently possible to observe the time profile of the increase of the concentration of the analyte in the interstitial water and in blood.

With the above and other objects in view there is also provided, in accordance with the invention, an apparatus for non-invasive determination of a measured variable of an analyte in a biological body, the apparatus comprising:

at least a first light source for irradiating the body with light from a wavelength range matched to an absorption signature of the analyte;

a speckle device for generating and observing a speckle pattern of coherent light scattered at the body; and a control unit configured to detect a change in the observed speckle pattern and to deduce a value of the measured variable of the analyte from the detected change.

In other words, the second-mentioned object is achieved by an apparatus for non-invasive determination of a measured variable of an analyte in a biological body, comprising at least a first light source for irradiating the body with light from a wavelength range matched to an absorption signature of the analyte, a speckle device for generating and observing a speckle pattern of coherent light scattered at the body and a control unit configured to detect a change in the observed speckle pattern and deduce a value of the measured variable of the analyte from the detected change.

Further advantageous embodiments emerge from the following variants and from the dependent claims directed to the apparatus. In this case, the advantages respectively mentioned in the case of the method can be transferred to the apparatus in an analogous fashion.

Preferably, the first light source is tunable in an IR (infra-red) sub-range, in particular in a wavelength range with wavelengths between 6 and 16 μm.

More preferably, the first light source is configured to emit light with a variable wavelength and the control unit is configured to actuate the first light source for varying the wavelength of the radiated-in light during the measurement and to detect the change in the speckle pattern for various wavelengths in each case.

Expediently, the first light source is configured to emit light with a variable power density and the control unit is configured to vary the light source for varying the power density of the radiated-in light during the measurement and to detect the change in the speckle pattern for various power densities in each case.

Advantageously, the light source is operable periodically with a modulation frequency. To this end, it is furthermore advantageous if the control unit is configured to detect the change in the speckle pattern synchronously with the modulation.

Preferably, a heart rate sensor is comprised, wherein the control unit is configured to detect the change in the speckle pattern synchronously with the heartbeat of the biological body.

In a further preferred alternative, the speckle device is configured to detect an image sequence of speckle images and the control unit is configured to detect the change in the speckle pattern by a comparison with the images from the recorded image sequence.

Preferably, the control unit is configured to establish the change in the speckle pattern as a contrast value in a difference image.

Expediently, the speckle device is configured to detect the image sequence of speckle images with an image refresh rate, wherein the control unit is configured to synchronize the image refresh rate with the modulation frequency and/or the heart rate of the biological body.

The speckle device is further advantageously configured to detect the change in the speckle pattern from the recorded image sequence as a function of time.

The control unit is configured to determine the concentration of glucose as a measured variable in an advantageous embodiment.

Other features which are considered as characteristic for the invention are set forth in the appended claims.

Although the invention is illustrated and described herein as embodied in a method and apparatus for non-invasive determination of a measured variable of an analyte in a biological body, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawing.

BRIEF DESCRIPTION OF THE DRAWING

The sole FIGURE of the drawing is a schematic view of an apparatus for non-invasive determination of a measured variable of an analyte in a human body according to the invention.

DETAILED DESCRIPTION OF THE INVENTION

Referring now to the FIGURE of the drawing in detail, there is shown an apparatus 1 for non-invasive determination of a measured variable of an analyte in a human body by means of the above-described method. In the particular case, the depicted apparatus 1 is embodied to determine the concentration of glucose in blood. By way of example, a forearm, as part of the human body 3, is irradiated with light matched to a specific absorption signature of the analyte—glucose in this case. In particular, a skin surface 4 is of interest here.

The apparatus 1 comprises a tunable semiconductor laser, in particular a quantum cascade laser, forming a first light source 6 for irradiating the body 3 with light 16 in the IR spectral range. The semiconductor laser emits light with wavelengths of between 8 μm and 11 μm, i.e. in the fingerprint range of the glucose molecule, in a tunable manner. Characteristic ring deformation vibrations are excited in this range.

Furthermore, the apparatus comprises a speckle laser forming a second light source 7, which continuously illuminates the skin surface 4 of the forearm 3 with light 18 at a fixed wavelength in the visible spectral range. The light 18 from the second light source 7 scattered by the skin surface 4 is observed by a camera 9. A speckle pattern 17, which has characteristic intensity minima and intensity maxima due to interference, results at the location of the camera 9 due to the different phase angles of the light rays scattered at the body 3. The speckle pattern 17 is very sensitive to changes on the skin surface 4, such as, for example, a deformation caused by radiating-in the excitation light. The second light source 7, the camera 9 and the corresponding imaging optics in the beam path of the light 18 together constitute a speckle device 10, by means of which a speckle pattern 17 of light 18 reflected at the skin surface 4 can be generated and observed.

By radiating-in the light 16, glucose contained in the body 3 and, in particular, in blood vessels close to the skin is excited specifically in the fingerprint range. As a result of this, there is local heating in the body 3 in the region of incident radiation, which leads to a characteristic deformation of the skin surface 4. This characteristic deformation 4 is identified as a change in the speckle pattern 17 in the image sequences recorded by the camera 9.

A control unit 13 is provided to detect the change in the speckle pattern 17. Said control unit is connected by way of corresponding control and data lines to the light sources 6, 7 and the camera 9. The control unit 13 actuates the first light source 6 to bring about periodic irradiation of the body 3. The absorption by glucose and, as a consequence, the deformation of the skin surface 4 is modulated in time by way of the periodic irradiation with a predetermined modulation frequency. The image refresh rate of the camera 9 is synchronized with the modulation frequency. The change in the speckle pattern 17 is established by forming differences of images in the image sequence, which images are recorded when the light source 6 is switched on and when the light source 6 is switched off. The power density of the light source 6 is additionally modulated. Furthermore, the wavelength range that can be generated by the light source 6 is run through. The change in the speckle pattern 17 is detected as a contrast in the difference image. The contrast in the difference image is taken as a measure for the concentration of the glucose.

Additionally, the modulation in the detected contrast as a consequence of the modulated optical power can be detected and evaluated. Likewise, the change in the difference image can be evaluated in a wavelength-specific manner. The evaluation accuracy can be increased further as a result of these additional items of information.

The second light source 7 generates polarized light 18. Interference light is masked by way of a spectral filter 20. There is an analysis of the polarization of the backscattered light 18 by means of the polarization discriminator 21, and so a polarization-dependent detection of the speckle pattern 17 is also made possible.

Furthermore, the apparatus 1 comprises a heart rate sensor 24. In particular, the control unit 13 is embodied to synchronize the image refresh rate of the camera 9 with the detected heart rate. It is possible to eliminate interfering measurement errors resulting from the pulsating skin surface 4 by observing the images with a fixed phase angle in relation to the heart rate in each case. A magnetic field generator 26 is additionally comprised. If a magnetic field is scattered into the body 3 by way of the magnetic field generator 26, glucose leads to a specific rotation of the polarization direction of the light 18 radiated-in due to the relatively high Verdet factor. The speckle pattern 17 can then additionally be observed and analyzed selectively from deeper layers of the skin by way of a polarization analysis.

The following is a summary list of reference numerals and the corresponding structure used in the above description of the invention:
1 Apparatus
3 Biological body
4 Surface
6 First light source
7 Second light source
9 Camera
10 Speckle device
13 Control unit
14 Output unit
16 Light
17 Speckle pattern
18 Light
20 Spectral filter
21 Polarization discriminator
24 Heart rate sensor
26 Magnetic field generator

The invention claimed is:

1. A method of non-invasive determination of a measured variable of an organic analyte in a biological body, the method comprising:

locally irradiating the body, in an automated manner, sufficient for causing at least some of the light to penetrate into the body and to be absorbed by the organic analyte, with light having a wavelength range between 6 µm and 16 µm matched to an absorption signature of the organic analyte, whereupon the body heats up at least locally as a result of an absorption by the organic analyte;
detecting a consequently occurring change in a speckle pattern of coherent light scattered at the body, and deducing from the change in the speckle pattern a value of the measured variable of the organic analyte.

2. The method according to claim 1, wherein the absorption by the organic analyte causes one or more changes selected from the group consisting of a deformation of the surface of the body, a change in the scattering properties of regions of the body close to the surface, and a change in a refractive index of regions of the body close to the surface, and the detecting step comprises detecting the one or more changes as the change in the speckle pattern.

3. The method according to claim 1, which comprises irradiating the body with light from an IR sub-range within a wavelength range with wavelengths between 7 µm and 11 µm.

4. The method according to claim 1, which comprises varying the wavelength of the radiated-in light during the measurement and detecting the change in the speckle pattern for different wavelengths in each case.

5. The method according to claim 4, which comprises alternately irradiating with light having a wavelength in an absorption maximum of the analyte and with light having a wavelength between the absorption maxima of the analyte.

6. The method according to claim 1, which comprises varying a power density of the radiated-in light during the measurement and detecting the change in the speckle pattern for different power densities in each case.

7. The method according to claim 1, which comprises irradiating with the light periodically with a modulation frequency.

8. The method according to claim 7, which comprises synchronizing a detection of the change in the speckle pattern with the modulation frequency of the light radiated-in periodically.

9. The method according to claim 1, which comprises detecting the change in the speckle pattern synchronously with a heart rate of the biological body.

10. The method according to claim 1, which comprises recording an image sequence of speckle patterns and detecting the change in the speckle pattern by a comparison of images from the recorded image sequence.

11. The method according to claim 10, which comprises establishing the change in the speckle pattern as a contrast value in a difference image.

12. The method according to claim 10, which comprises recording the images in the image sequence with an image refresh rate and synchronizing the image refresh rate with a modulation frequency of the light that is radiated-in periodically and/or with a heart rate of the biological body.

13. The method according to claim 10, which comprises detecting the change in the speckle pattern from the recorded image sequence as a function of time.

14. The method according to claim 1, which comprises irradiating the body with polarized light.

15. The method according to claim 13, which comprises observing the speckle pattern in dependence on a polarization of the light scattered on the body and determining the change in the speckle pattern for a specific polarization in each case.

16. The method according to claim 1, which comprises additionally generating a magnetic field at a location where the body is irradiated with light.

17. The method according to claim 1, which comprises generating the light with a tunable light source and generating the light matched to the absorption signature of the analyte.

18. The method according to claim 17, wherein the tunable light source is a semiconductor laser.

19. The method according to claim 1, which comprises generating the light with a first coherent light source matched to the absorption signature of the analyte and observing the speckle pattern in the light of the first light source after scattering back from the body.

20. The method according to claim 19, which comprises irradiating the body with light from a second coherent light source and observing the speckle pattern in the light of the second light source after scattering back from the body.

21. The method according to claim 20, wherein the light from the second coherent light source is in a visible spectral range.

22. The method according to claim 1, wherein the analyte is glucose and the measured variable is a concentration of the glucose.

23. An apparatus for non-invasive determination of a measured variable of an organic analyte in a biological body, the apparatus comprising:

at least a first light source for irradiating the body with light from in a wavelength range between 6 μm and 16 μm matched to an absorption signature of the organic analyte, wherein the irradiated light is sufficient to cause at least some of the light to penetrate into the body and to be absorbed by the organic analyte, whereupon the body heats up at least locally as a result of an absorption by the organic analyte;

a speckle device for generating and observing a speckle pattern of coherent light scattered at the body; and a control unit configured to detect a change in the observed speckle pattern and to deduce a value of the measured variable of the organic analyte from the detected change.

24. The apparatus according to claim 23, wherein said first light source is configured to emit polarized light.

25. The apparatus according to claim 24, wherein said speckle device comprises a polarization discriminator and said control unit is configured to detect the change in the speckle pattern for a specific polarization in each case.

26. The apparatus according to claim 23, which further comprises a magnetic field generator for generating a magnetic field at a location where the body is irradiated by light.

27. The apparatus according to claim 23, wherein said first light source is a tunable light source.

28. The apparatus according to claim 27, wherein said tunable light source is a semiconductor laser.

29. The apparatus according to claim 23, wherein said first light source is configured to generate coherent light and wherein said speckle device is configured to generate and observe the speckle pattern in the light of said first light source scattered at the body.

30. The apparatus according to claim 29, which further comprises a second light source for generating coherent light and wherein said speckle device is configured to generate and observe the speckle pattern in the light of said second light source scattered at the body.

31. The apparatus according to claim 30, wherein said second light source is configured to generate light in a visible spectral range.

\* \* \* \* \*